United States Patent [19]

Barry

[11] Patent Number: 4,554,826
[45] Date of Patent: Nov. 26, 1985

[54] AUTOMATIC DEPTH-DETERMINING AQUATIC SAMPLING DEVICE

[76] Inventor: Judith A. Barry, 4515 W. 15th Ave., Vancouver, B.C., Canada, V6R 3B3

[21] Appl. No.: 343,397

[22] Filed: Jan. 28, 1982

[51] Int. Cl.⁴ .............................................. G01N 1/00
[52] U.S. Cl. .............................. 73/170 A; 73/864.63; 73/864.67
[58] Field of Search ........... 73/170 A, 864.64, 864.63, 73/864.67

[56] References Cited

U.S. PATENT DOCUMENTS

| | | | |
|---|---|---|---|
| 3,176,517 | 4/1965 | Chelminski | 73/170 A |
| 3,339,417 | 9/1967 | Richard | 73/170 A |
| 3,513,709 | 5/1970 | Pullos | 73/863.01 |

*Primary Examiner*—Donald O. Woodiel

[57] ABSTRACT

An apparatus for the collection of water or other data from the aquatic environment, the apparatus being programmable to make such collections at any desired depths as it descends, and being capable of ascending to the surface under its own power, all functions being performed independently of any external connections or commands. The apparatus possesses a multifunctional mechanism which not only monitors the time and depth of the apparatus' descent, but also actuates the sequential sealing of the sampling chambers at each pre-programmed sampling depth and the release of ballast upon completion of sampling. This mechanism monitors time by monitoring the rate and distance of travel of a piston operating under constant force where the piston's rate of travel is governed by the rate at which it can draw water through an orifice.

4 Claims, 8 Drawing Figures

AUTOMATIC DEPTH-DETERMINING AQUATIC SAMPLING DEVICE

State of the art devices for collecting water and other data from specific depths (U.S. Pat. Nos. 4,002,066, 3,892,130, 3,513,709, 3,339,417 and 3,176,517) require the use of line both as a means of measuring depth and as a means of lowering and raising the device. This method of determining depth is subject to essentially indeterminate errors, such as stretching of the line due to its own weight as well as the equipment attached, and angling of the line due to currents. Slippage of the metered winch which delivers steel cable introduces yet another indeterminate error in the measurement of depth. U.S. Pat. No. 3,513,709 suggests a solution in the use of a disc which ruptures when a predetermined pressure of the ambient water is attained after the device is lowered by cable to the approximate depth. The above invention is exemplary of conventional devices in that the mechanisms for determining depth and triggering collections are independent of one another and constitute two different steps in operation, the latter mechanism comprising a command external to the device such as a weighted messenger slid down the line, electrical pulses or acoustical signals.

When collections are made in any but the most shallow depths, steel cable delivered from a metered winch is required. The dead weight stress on the cable often attains one-half ton, and may exceed one ton when the vessel carrying the cable rolls due to sea action, making the use of a vessel of substantial size mandatory. Such vessels are operated at tremendous cost. In addition, conventional devices are limited to the depths to which they can descend by the length of cable carried on any particular vessel; this length is in itself limited due to the sheer dead weight of the cable. If a longer cable is necessary, either a new vessel with a longer cable must be obtained, or a new cable installed; either way, a certain length cannot be surpassed without requiring an increase in the diameter, which results in a further weight increase.

This invention seeks to reduce the high cost and complexity inherent in state of the art systems for the collection of substances and data from the aquatic environment. Accordingly, the principal object of the invention is to provide a selfcontained apparatus which is independent of physical connections or operational commands from the surface by automatically and continuously monitoring its depth as it descends, collecting water and other data at predetermined depths, and by being completely programmable for descent, collection and ascent. A further object of the invention is to employ the same mechanism which monitors the depth of the apparatus to mechanically actuate both sample collection and the apparatus' self-ascent. Another characteristic of the invention is that it can operate in any range of depths with a simple interchange of parts.

These and other objects and features of the invention will become more readily apparent and understood from the following specification and accompanying drawings. Water is anticipated to be the most commonly collected substance by this invention, while temperature and conductivity are examples of customarily collected data. In the preferred and modified embodiments below, water and temperature are being collected.

Figure 1:
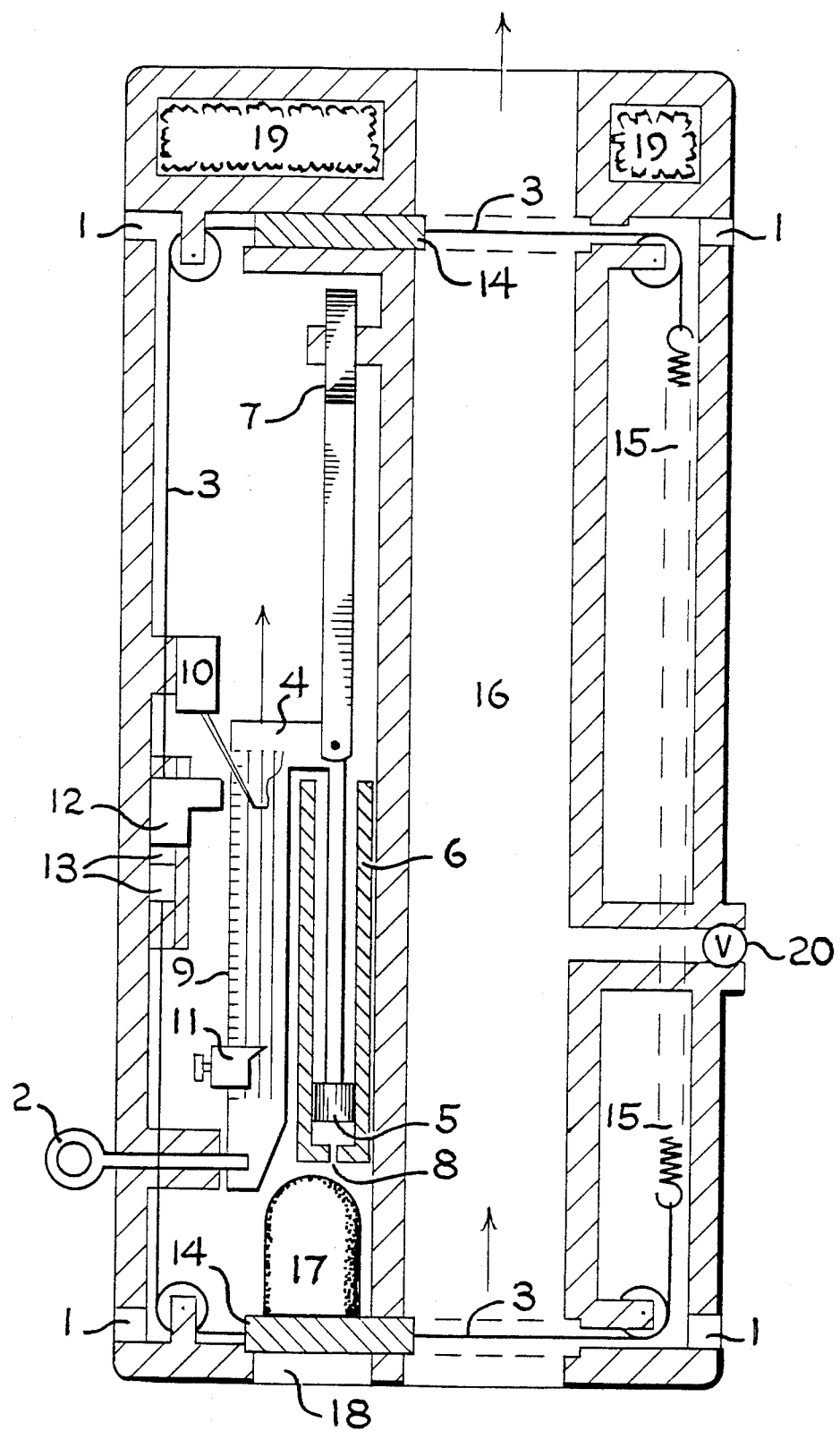
FIG. 1 is a view of a longitudinal section of the preferred embodiment of the invention for the collection of a single water sample from a single depth.

Referring to FIG. 1, the preferred embodiment of the invention may be programmed to take one water sample at any depth included on its depth scale. The operator submerges the apparatus in the water with its ballast end downward, allowing entrapped air to escape through vent ports 1, then the operator removes activating pin 2 to release restriction of movement from "U" shaped member 4. The apparatus is then released to begin its free-fall descent through the water, at a rate of travel that is constant and predictable throughout the descent. Piston 5, located inside of time sensing cylinder 6, is attached to one end of "U" shaped member 4, and constant force spring 7 is attached to the opposite end. Removal of activating pin 2 allows constant force spring 7 to draw piston 5 through time sensing cylinder 6 at a uniform rate, drawing water into cylinder 6 through metering orifice 8 as it moves. The rate at which piston 5 and "U" shaped member 4 travel is a function of the diameter of metering orifice 8 and is constant and predictable. It is the constant and predictable rate of travel of piston 5 (and "U" shaped member 4) that provides the basis by which time and depth are monitored throughout the apparatus' descent, through the relation of rate to time as given in equations (1) and (2), where rate is defined as distance divided by time:

$$(\text{distance of piston travel}/\text{rate of piston travel}) = \text{time elapsed from surface} \quad (1)$$

$$\text{rate of apparatus travel} \times \text{time elapsed from surface} = \text{distance of travel from surface} = \text{depth} \quad (2)$$

Equations (1) and (2) permit the distance of travel of piston 5 (and "U" shaped member 4) to be translated into time and depth of the apparatus' descent. In this way depth scale 9, printed on a stable material such as mylar and attached to one edge of "U" shaped member 4, is calibrated in units of depth (and time if desired). Note from equations (1) and (2) that the maximum depth at which collection can occur is limited by the maximum length of time required by piston 5 to travel the full length of cylinder 6. Therefore the range of sampling depths can be varied to span all depths from a shallow lagoon to the deepest abyss in the ocean by varying the time in which piston 5 undergoes its maximal travel. There are two means by which this can be executed: by modifying the rate at which piston 5 travels, for instance by varying the diameter of metering orifice 8, or by modifying the rate at which the apparatus descends, which could be effected by altering the mass of ballast 17. Acheiving a more rapid descent is the preferred means when sampling in very deep water in order to avoid reducing the diameter of orifice 8 to such a degree that it easily becomes clogged by solids in the water. Each depth range correlating to a time required for maximal travel of piston 5 has a corresponding calibrated depth scale 9, these depth scales being interchangeable to match whatever depth range has been chosen for a particular collection operation. Also inscribed on depth scale 9 is a temperature scale, upon which the temperature is continually recorded as a function of depth by means of an inscriber driven by a standard temperature sensor 10.

Figure 2:
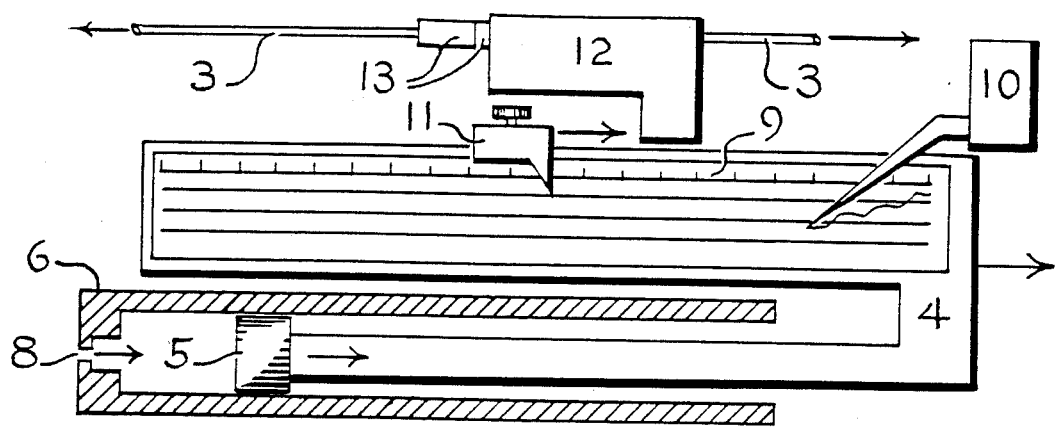
FIG. 2 is an enlarged view of the time monitoring element of the preferred embodiment in the same section as that in FIG. 1.

Prior to release of the apparatus by the operator, an adjustable triggering stop 11 is locked at the desired sampling depth (or time) along depth scale 9 by means of a set screw. When "U" shaped member 4 has travelled the pre-programmed length of time toward constant force spring 7, triggering stop 11 will impinge on trigger bar 12 causing the release of locking blocks 13. Each of the two locking blocks 13 is attached by flexible, free-running lines 3 to the edges of gate valves 14 while the opposite edge of each gate valve 14 is attached to extension spring 15 by flexible lines 3. FIG. 2 provides an enlargement of the time-monitoring and triggering mechanism for greater clarity, through to the involvement of trigger bar 12.

Figure 3:
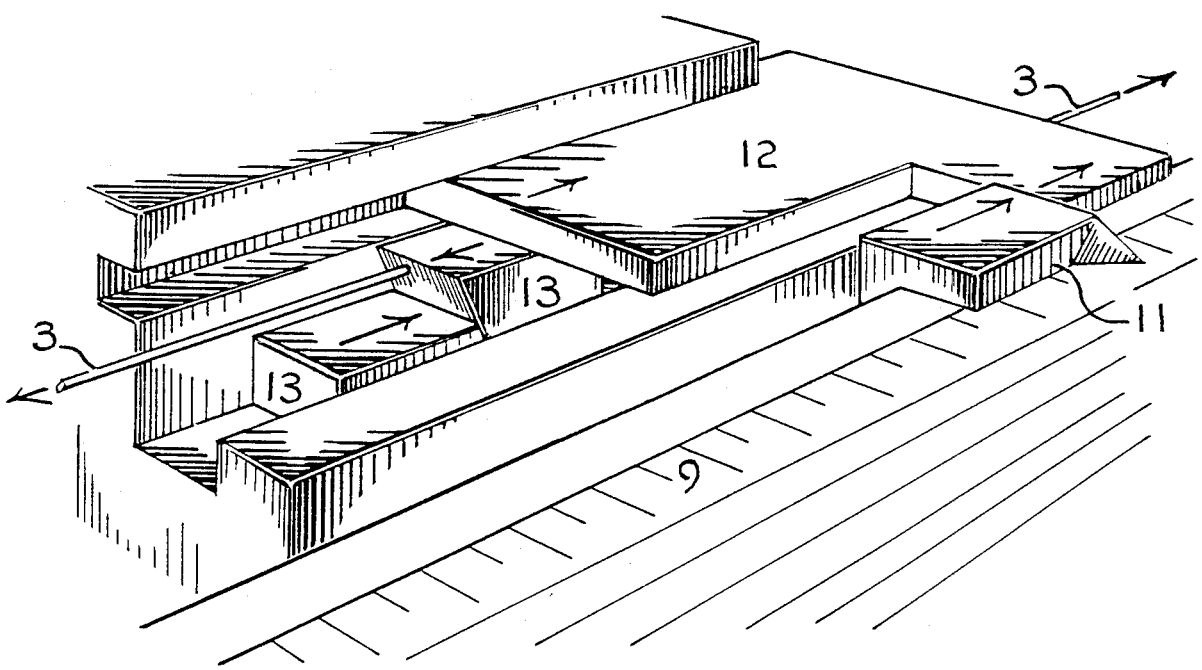
FIG. 3 is a perspective view of the triggering element of the same preferred embodiment.

FIG. 3 details the sequence of events by which the travel of triggering stop 11 activates the sealing of sample chamber 16. Referring to FIG. 3, both locking blocks 13 are confined to a groove so they cannot move laterally, and the only manner by which they can become unlocked is for the upper of the two locking blocks 13 to move up and over the lower locking block. Vertical movement of the upper locking block is prevented because it lies beneath trigger bar 12, which is itself prevented from upward movement by its confinement to sliding tracks. When triggering stop 11 impinges on trigger bar 12 it moves along the upper locking block 13 until it is no longer in contact with this block. Clearance of trigger bar 12 over upper block 13 occurs precisely at the set depth of sampling, allowing upper block 13 to move up and over lower block 13, so the blocks are pulled apart in opposite directions by the force of extension spring 15. The faces of the locking blocks 13 that are in contact with each other are angular rather than vertical so that some of the force acting on the upper block by extension spring 15 is translated into an upward motion to assure a clean separation of the blocks.

Referring again to FIG. 1, as described previously, when the apparatus had descended to a depth where piston 5, "U" shaped member 4 and triggering stop 11 have travelled a distance such that locking blocks 13 are allowed to separate, the force of extension spring 15 draws gate valves 14 across the ends of sampling chamber 16 to trap a sample of water from that depth. Ballast 17, which rests on top of the lower gate valve 14, will drop through ballast hole 18 as the gate valve upon which it was resting moves from beneath it. Release of the ballast 17, in combination with flotation material 19 located on top of the apparatus, renders the apparatus positively bouyant so it rises to the surface. Once the operator retrieves the floating apparatus, the water sample is removed from the sample chamber 16 through discharge valve 20.

The modified embodiment of the invention illustrated in FIGS. 4 through 8 has eleven sampling chambers as opposed to the single chamber in the preferred embodiment. The operating principle of the modified embodiment is essentially identical to that of the preferred embodiment except that movement of the depth scale and the gate valves has been translated into rotational motion in the modified embodiment as opposed to the linear motion used in the preferred embodiment.

Figure 4:
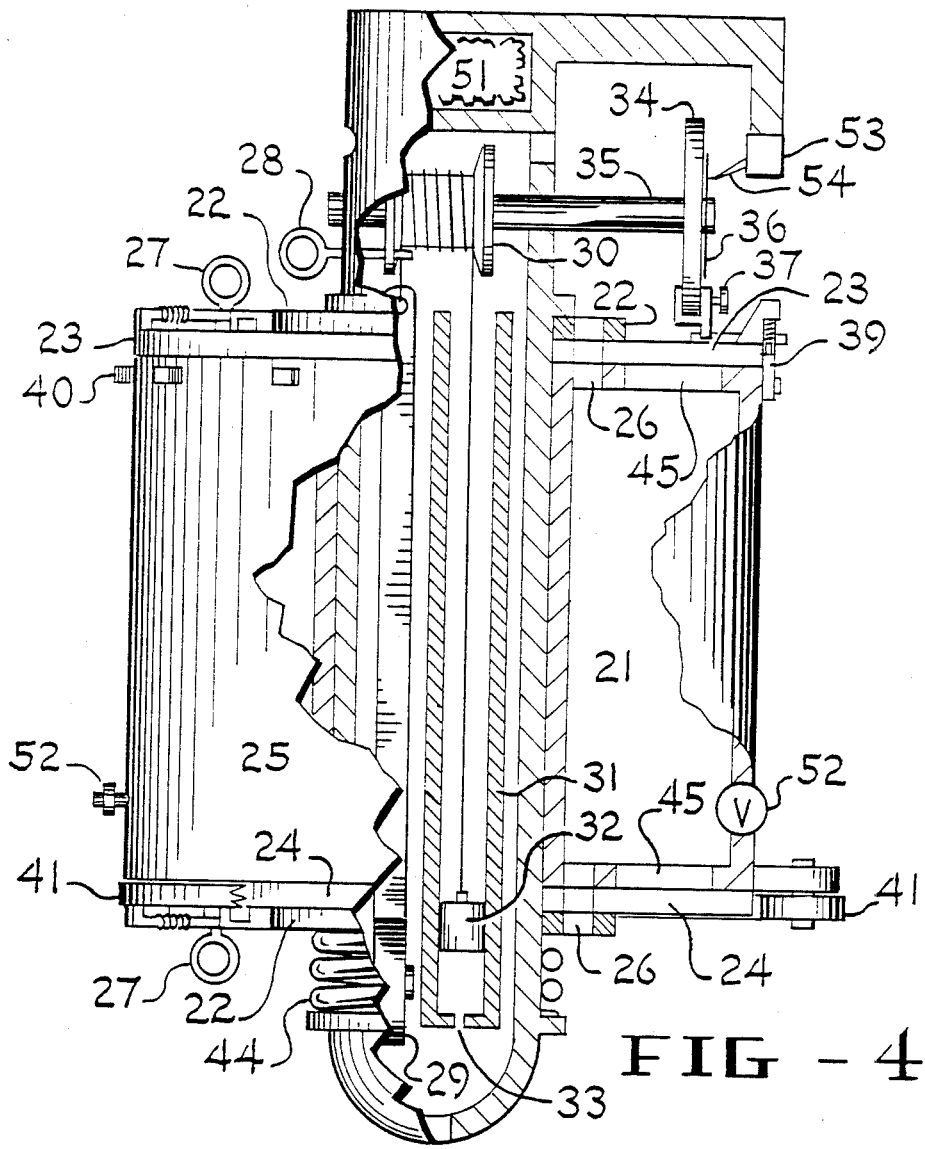
FIG. 4 is a perspective side view of the modified embodiment of the invention for the collection of a plurality of water samples from a plurality of depths, in which portions of the exterior view of the apparatus have been cut away to provide a partial longitudinal section view of the interior as well.

Referring to FIG. 4, eleven sampling chambers 21 of equal size and configuration are incorporated in a single rigid sampling chamber assembly 25. Against the top and bottom ends of sampling chamber assembly 25 are gate valves 23 and 24, respectively, and against each gate valve is a charging valve 22; the integrity of the seal between valves 22, 23 and 24 and sampling chamber assembly 25 is maintained by a compression spring 44. Charging ports 26 are located in all valves 22, 23 and 24 and in the assembly 25 such that when all the charging ports 26 are aligned water floods through charging ports 26 into sampling chambers 21. This flooding, in conjunction with the apparatus' ballast, renders the apparatus negatively bouyant. Flooding constitutes the first step in preparing the apparatus for free-fall descent, followed by removal of charging pin 27 to allow charging valves 22 to rotate their ports 26 out of alignment with the other ports 26 into a closed position. The twelfth chamber contained in assembly 25 is an identically structured chamber which functions as an open chamber during ascent (discussed later). Prior to releasing the apparatus for descent, the operator removes activating pin 28 to allow constant force spring 29 to pull on the line attached to its power end so the line takes several turns around power drum 30, becoming taut and priming power drum 30 for operation. The other end of the line passes through time sensing cylinder 31 and attaches to piston 32. With the eleven sampling depths pre-programmed on the apparatus before it was placed in the water, the apparatus is at this point primed to perform all of its functions.

During free-fall descent of the apparatus, the travel of piston 32 operating at a constant and predictable rate under the force of constant force spring 29 draws water through metering orifice 33 at a constant and predictable rate dependent upon the diameter of orifice 33. As spring 29 winds up and piston 32 travels through cylinder 31, power drum 30, axel 35 and the depth scale disc 34 attached to the end of axel 35 all rotate. The monitoring of time and depth is completely analogous to that described for the preferred embodiment, including calibration of the interchangeable depth scale inserts 26 according to the principals in equations (1) and (2), and the variations in the range of sampling depths. As noted previously, however, the motion of the interchangeable depth scale insert 26 is rotational in the modified embodiment rather than linear as in the preferred embodiment.

Eleven adjustable triggering stops 37 corresponding to the eleven sampling chambers 21 are positioned around the circumference of depth scale disc 34 at the eleven desired sampling depths. Each triggering stop 37 is set on the disc 34 by means of a locking screw to trigger collection of a sample at any depth included on the interchangeable depth scale insert 36 being employed for that particular collection mission. The continuous recording of temperature as a function of depth in this embodiment is provided by a standard temperature sensor 53 driving a recording inscriber 54 set on the interchangeable depth scale insert 36. The inscriber 54 begins at the surface on the zero depth radial on the temperature scale of insert 36, inscribing a radial temperature profile as a function of depth as depth scale disc 34 and insert 36 rotate during descent. When an adjustable triggering stop 37 on the rotating disc 34 has travelled its designated time corresponding to one of the sampling depths, it impinges on a triggering mechanism that disengages trigger dog 39 from an indexing lug 40. The contact of lug 40 against dog 39 prevents sampling chamber assembly 25 from rotating, under the force of main drive spring 41, with respect to gate valves 23 and 24 and charging valves 22.

Figure 5:
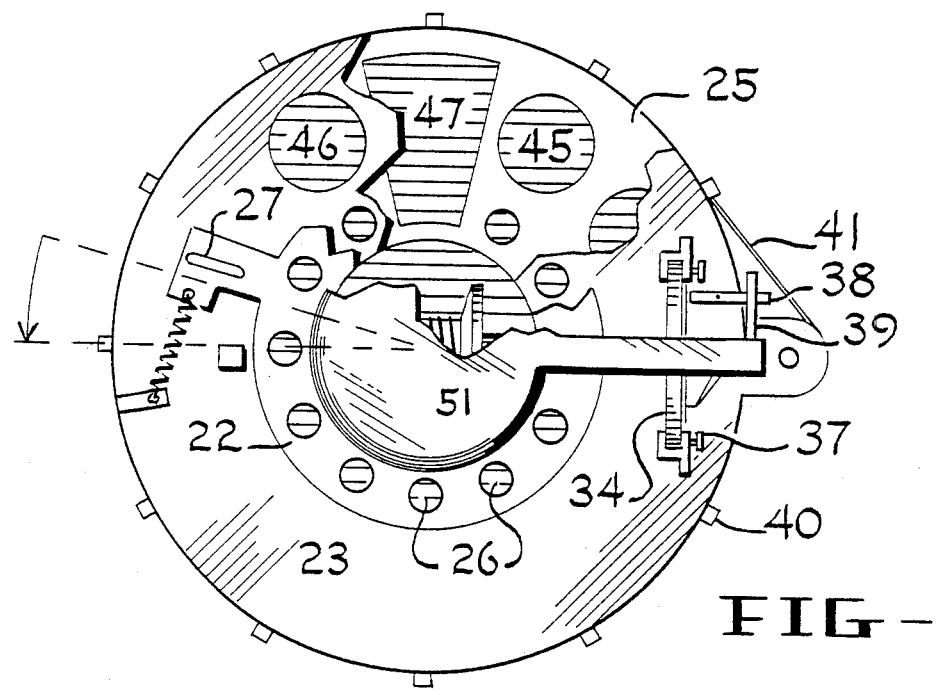
FIG. 5 is a perspective top view of the modified embodiment in which portions of the valving have been drawn cut away to illustrate the arrangement of the valving with respect to the sampling chamber assembly.

Refer to FIG. 5 for a view of the apparatus which illustrates the manner in which the valves 22, 23 and 24 and sampling chamber assembly 25 rotate relative to one another in order to seal off ports 26 following flooding and to collect the water samples. From this figure it can be seen that the means by which charging valves 22 rotate to disalign charging ports 26 is by force of springs attached to the arm of each valve 22, which are permitted to compress upon removal of charging pin 27. When the first sampling depth is attained, the first triggering stop 37 on depth scale disc 34 impinges on trigger lever 38, displacing it so that it disengages trigger dog 39 from its locked position against an indexing lug 40. The release of lug 40 frees sampling sampling chamber assembly 25 to rotate under the force of main drive spring 41 by one twelfth of a revolution before trigger lever 38 and trigger dog 39 lock back into position and engage the next in line of the twelve equally spaced indexing lugs 40 on assembly 25. This one-twelfth of a revolution of assembly 25 with respect to gate valves 23 and 24 causes the single aperature 46 in each gate valve to be aligned with the sampling ports 45 at each end of the next sampling chamber 21 in sequence, allowing an unobstructed flow of water through this sampling chamber. Therefore, the rotation of gate valves 23 and 24 with respect to sampling chamber assembly 25 also seals the sampling chamber 21 that had been aligned with gate valve aperatures 46 prior to rotation. In summary, when rotation of the assembly 25 is triggered at a certain sampling depth, water from that depth is sealed inside the chamber that previously had been open to a free flow of water, while the next sampling chamber 21 in sequence becomes aligned with the gate valve aperatures 46 to receive an unobstructed flow of water in preparation for collection at the next sampling depth. This sequence of events is repeated for each sampling chamber 21 until the eleventh chamber is sealed, at which time the gate valve aperatures 46 become aligned with ascent chamber 47 rather than any of the sampling chambers 21. This induces the ballast to be dropped (as discussed later) and the highly bouyant flotation material 51 compels the apparatus to the surface.

Figure 6:
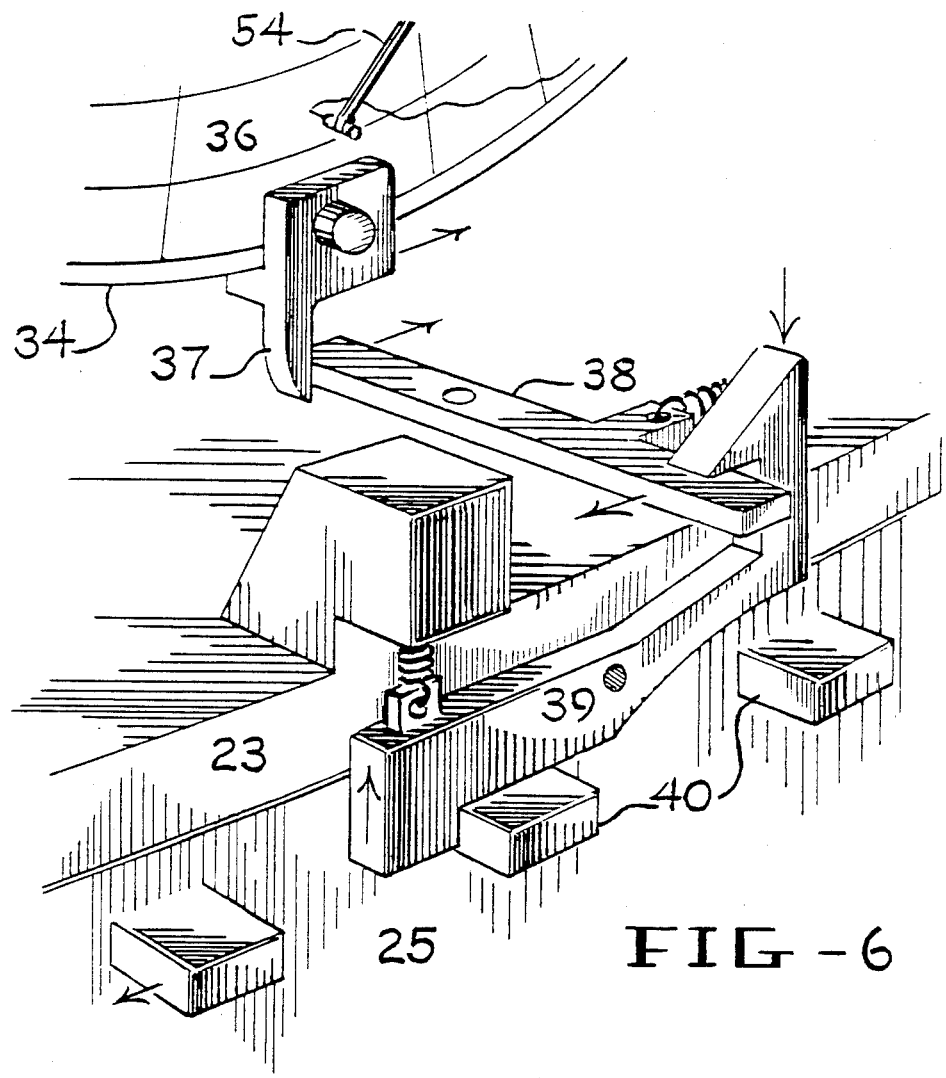
FIG. 6 is a perspective view of the triggering mechanism of the modified embodiment.

Referring to FIG. 6 for a more detailed view of the triggering mechanism, sampling chamber assembly 25 is restrained from rotating in the direction indicated by the arrow by the incursion of indexing lug 40 against trigger dog 39. Trigger dog 39 is mounted on top gate valve 23 by a pin and has an upward force operating on the end engaging lug 40 which is prevented from displacing this end of dog 39 by the latch at the dog's other end which is engaged to trigger lever 38. Trigger lever 38 can also pivot about its mounting pin, but is restrained into the engaged position with dog 39 by a helical extension spring until triggering stop 37 makes contact with the non-engaged end of lever 38. Upon contact, the movement of stop 37 pushes along the non-engaged end of lever 38 in the direction indicated by the arrow, displacing the other end of lever 38 from dog 39. The end of trigger dog 39 engaging lug 40 can then be pulled upward by the spring, releasing lug 40 so the sampling chamber assembly 25 is free to rotate relative to gate valves 23 and 24. The next indexing lug 40 impinges on the camming surface of dog 39 to impel the latch end of dog 39 upward to reengage trigger lever 38, which has been pulled back into the pre-sampling position by the helical extension spring. Thus trigger dog 39 is in its locked, pre-sampling position ready to reengage the approaching indexing lug 40.

Figure 7:
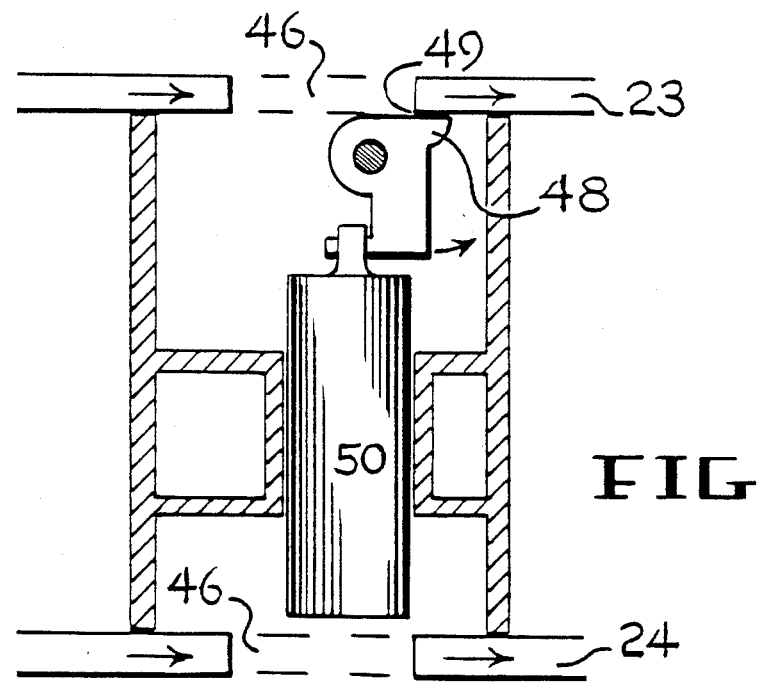
FIG. 7 is a longitudinal section of the ballast system of the modified embodiment.

When the eleventh sampling chamber 21 has been sealed by gate valves 23 and 24 and the gate valve aperatures 46 are aligned with ascent chamber 47, the ballast is dropped as illustrated by FIG. 7. A pivotally mounted ballast latch 48 remains hooked onto ballast 50 as along as the upper surface of the latch is pressed against top gate valve 23. However, once the leading edge 49 of the top gate valve aperature 46 clears ballast latch 48 upon the final rotation of assembly 25, the ballast latch 48 pivots upward on its pin to release ballast 50 to fall through bottom gate valve aperature 46.

Figure 8:
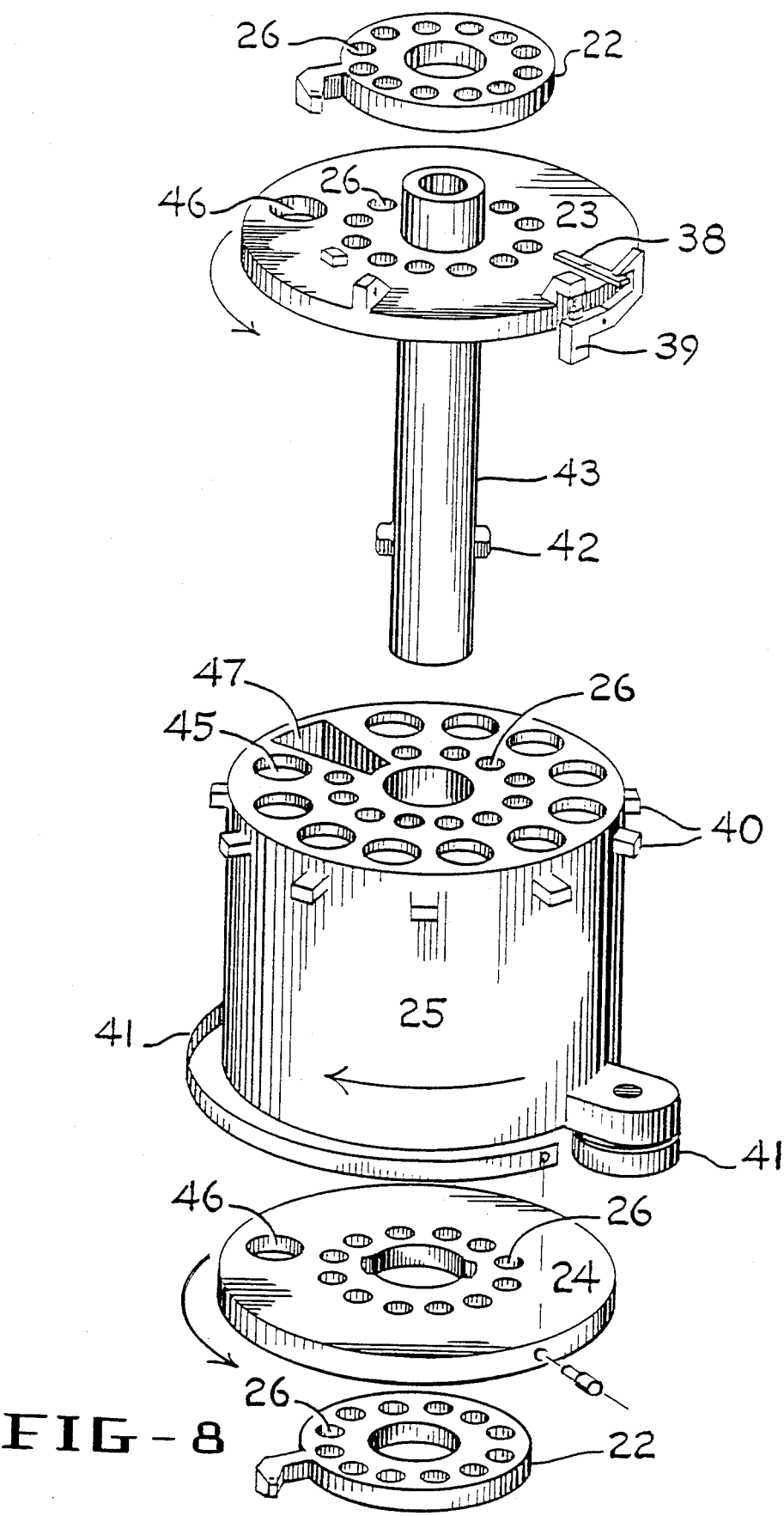
FIG. 8 is an exploded view of the arrangement of the sampling chamber assembly and associated valves which achieves the sequential collection of water samples by the modified embodiment.

FIG. 8 provides an exploded view of the valving, with many of the other details of the apparatus omitted for clarity. Top gate valve 23 has no freedom of motion about hub 43, either vertically or rotationally; the water collection and ballast release triggering mechanism is attached to this valve 23. Bottom gate valve 24 keys into spline 42 to secure it from rotational movement, but it can be moved vertically along hub 43. Charging valves 22 undergo no movements independently of gate valves 23 and 24 once the charging valves 22 are rotated after flooding to seal off charging ports 26. Main drive spring 41, mounted at its coiled end on sampling chamber assembly 25, rotates assembly 25 about hub 43 relative to all the valves 22, 23 and 24 by having its other end attached to bottom gate valve 24 by a spring pin. Rotation of assembly 25 is restricted by the incursion of an indexing lug 40 against trigger dog 39, except during sample collection when the triggering mechanism releases the lug 40 being restrained. All twelve of the chambers contained in assembly 25 have the same configuration, the only difference between sampling chambers 21 and the ascent chamber 47 being that the latter is not bound on its ends by plates bearing a sampling port 45 and charging port 26.

Referring again to FIG. 4, release of ballast 50 renders the apparatus positively bouyant by virtue of the very low density material comprising flotation element 51, compelling the apparatus to ascend to the surface. Upon retrieval of the apparatus by the operator, the water samples are drained from sampling chambers 21 through discharge valves 52.

Various adaptations and modifications of this invention may be suggested based on the principles employed in the embodiments described here for sake of illustration. It is therefore understood that within the scope of the claims tendered below, other applications of this invention than those specifically described are feasible.

I claim:

1. An apparatus for collecting water at predetermined depths in water comprising: the means for the apparatus to continually monitor its depth in water through the relation of velocity to time, where velocity is known from the constant and predictable rate with which the apparatus undergoes freefall descent, and time is measured from the rate and distance of travel of a piston operating under constant force, where the piston's constant and predictable rate of travel is governed by the diameter of the metering orifice located in the bottom base of the cylinder housing the piston, the orifice controlling the rate at which the piston is able to draw water into the cylinder; means to pre-program sampling depth prior to descent of the apparatus by setting an adjustable triggering stop or series of stops onto a calibrated depth scale, the calibrations derived from the constant and predictable time of travel of the piston; means by which the travel of the piston causes motion of the depth scale relative to an inscriber on a standard temperature sensor, causing a continuous plot of temperature as a function of depth to be inscribed on the depth scale; means to vary the range of depths in which collection occurs by varying the time in which the piston travels its maximum distance by modifying the rate at which either the piston or the apparatus travels, these variations effected by modifying such parameters as the amount of ballast or the diameter of the metering orifice, where each depth range has a corresponding interchangeable depth scale; a sampling chamber or assembly of chambers equipped at both ends with gate valves which seal a chamber for sample collection, these gate valves urged into the post-sampling position by spring force; a mechanical device which restrains the gate valves in their pre-sampling position until released at the time of sample collection; means to collect a water sample by attaching the calibrated depth scale to the piston so that the depth scale and its attached triggering stops or series of stops travel at the same constant and predictable rate as does the piston, this travel causing a triggering stop to impinge on the mechanical device restraining the gate valves in their pre-sampling position, this impingement releasing the restraint on the valves so they assume their post-sampling position and seal the sample chamber which corresponds to that sampling depth; means for releasing a ballast following completion of the final collection, the release being pre-programmed on the depth scale in the same manner as that to pre-program the collection of water samples; a sufficient amount of very low density material as to render the apparatus positively bouyant upon release of the ballast, compelling the apparatus to ascend to the surface unaided by forces external to the apparatus.

2. An apparatus as in claim 1 for collection of a single water sample where the mechanical device for restraining the gate valves in their pre-sampling, or open, position comprises a pair of locking blocks, with impingement of the triggering stop on the locking block assembly displacing the blocks from 3. An apparatus as in claim 1 for collection of a plurality of water samples where the sampling chamber assembly and mechanical device for restraining the gate valves in their presampling position comprise: an assembly consisting of a circular array of water sampling chambers equipped at both ends with gate valves, each gate valve containing a single aperature to align in the open position with one sampling chamber at a time; means by which the assembly of sampling chambers is induced under spring force to rotate relative to the gate valves at the time of sampling to seal the open chamber and open the next chamber in sequence in preparation for collection at the next sampling depth; means by which the sampling chamber assembly is restrained from rotating during travel to the next sampling depth by a mechanical device engaging a lug on the assembly; means by which the lug is disengaged at the sampling depth by impingement of a triggering stop on the mechanical device engaging the lug; repitition of the sequence of events comprising collection until all samples are collected.

4. An apparatus for carrying instruments which collect data and samples of any nature at predetermined depths in water comprising: the means for the apparatus to continually monitor its depth in water through the relation of velocity to time, where velocity is known from the constant and predictable rate with which the apparatus undergoes free-fall descent, and time is measured from the rate and distance of travel of a piston operating under constant force, where the piston's constant and predictable rate of travel is governed by the diameter of the metering orifice located in the bottom base of the cylinder housing the piston, the orifice controlling the rate at which the piston is able to draw water into the cylinder; means to pre-program sampling depth prior to descent of the apparatus by setting an adjustable stop or series of stops onto a calibrated depth scale, the calibrations derived from the constant and predictable time of travel of the piston; means by which the travel of the piston causes motion of the depth scale relative to an inscriber on a standard temperature sensor, causing a continuous plot of temperature as a function of depth to be inscribed on the depth scale; means to vary the range of depths in which collection occurs by varying the time in which the piston travels its maximum distance by modifying the rate at which either the piston or the apparatus travels, these variations effected by modifying such parameters as the amount of ballast or the diameter of the metering orifice, where each depth range has a corresponding interchangeable depth scale; means for releasing a ballast following completion of the final collection, the release being pre-programmed on the depth scale in the same manner as that to pre-program the various collections; a sufficient amount of very low density material as to render the apparatus positively bouyant upon release of the ballast, compelling the apparatus to ascend to the surface unaided by forces external to the apparatus.

* * * * *